US 11,978,856 B2

(12) United States Patent
Han et al.

(10) Patent No.: US 11,978,856 B2
(45) Date of Patent: May 7, 2024

(54) NON-AQUEOUS ELECTROLYTE SOLUTION FOR LITHIUM SECONDARY BATTERY

(71) Applicant: LG Energy Solution, Ltd., Seoul (KR)

(72) Inventors: Jung Gu Han, Daejeon (KR); Jung Min Lee, Daejeon (KR); Chul Haeng Lee, Daejeon (KR); Chul Eun Yeom, Daejeon (KR); Kyung Mi Lee, Daejeon (KR)

(73) Assignee: LG Energy Solution, Ltd., Seoul (KR)

(*) Notice: Subject to any disclaimer, the term of this patent is extended or adjusted under 35 U.S.C. 154(b) by 0 days.

(21) Appl. No.: 17/914,601

(22) PCT Filed: Nov. 17, 2021

(86) PCT No.: PCT/KR2021/016905
§ 371 (c)(1),
(2) Date: Sep. 26, 2022

(87) PCT Pub. No.: WO2022/260222
PCT Pub. Date: Dec. 15, 2022

(65) Prior Publication Data
US 2024/0063435 A1    Feb. 22, 2024

(30) Foreign Application Priority Data

Jun. 8, 2021 (KR) .................. 10-2021-0073895

(51) Int. Cl.
*H01M 10/0567* (2010.01)
*C07D 319/06* (2006.01)
*H01M 10/052* (2010.01)

(52) U.S. Cl.
CPC ...... *H01M 10/0567* (2013.01); *C07D 319/06* (2013.01); *H01M 10/052* (2013.01); *H01M 2300/0042* (2013.01)

(58) Field of Classification Search
CPC ........... H01M 10/0567; H01M 10/052; H01M 2300/0042; C07D 319/06
See application file for complete search history.

(56) References Cited

U.S. PATENT DOCUMENTS

| 7,033,707 | B2 | 4/2006 | Gan et al. |
| 2003/0162098 | A1 | 8/2003 | Gan et al. |
| 2007/0178379 | A1 | 8/2007 | Tamura et al. |
| 2007/0243471 | A1 | 10/2007 | Takahashi |
| 2010/0305281 | A1 | 12/2010 | Fujiwara et al. |
| 2016/0336614 | A1 | 11/2016 | Hatta et al. |
| 2017/0200976 | A1 | 7/2017 | Nakazawa et al. |
| 2018/0166746 | A1 | 6/2018 | Shimamoto et al. |
| 2019/0267670 | A1 | 8/2019 | Xu et al. |
| 2020/0044287 | A1 | 2/2020 | Kim et al. |
| 2020/0251777 | A1 | 8/2020 | Lim et al. |

FOREIGN PATENT DOCUMENTS

| CN | 100999515 A | 7/2007 |
| EP | 3893312 A1 | 10/2021 |
| JP | 2000091162 A | 3/2000 |
| JP | 2006086058 A | 3/2006 |
| JP | 2007287518 A | 11/2007 |
| JP | 4564237 B2 | 10/2010 |
| JP | 2014072050 A | 4/2014 |
| JP | 5952264 B2 | 7/2016 |
| JP | 2019535101 A | 12/2019 |
| JP | 2020194782 A | 12/2020 |
| KR | 100407486 B1 | 12/2003 |
| KR | 20160111378 A | 9/2016 |
| KR | 20190059256 A | 5/2019 |
| KR | 20200076230 A | 6/2020 |
| KR | 20200089623 A | 7/2020 |
| KR | 102270869 B1 | 7/2021 |
| WO | 2015093532 A1 | 6/2015 |

OTHER PUBLICATIONS

International Search Report for Application No. PCT/KR2021/016905 dated Mar. 2, 2022, pp. 1-3. [See p. 2, categorizing the cited references].
Extended European Search Report for Application No. 21930604.0 dated Nov. 29, 2023, pp. 1-5.
Sanders, D.P. et al., "A Simple and Efficient Synthesis of Functionalized Cyclic Carbonate Monomers Using a Versatile Pentafluorophenyl Ester Intermediate", Journal of The American Chemical Society, vol. 132, No. 42, Sep. 30, 2010 (Sep. 30, 2010), pp. 14724-14726, XP055242220.

*Primary Examiner* — James Lee
(74) *Attorney, Agent, or Firm* — Lerner David LLP

(57) ABSTRACT

A non-aqueous electrolyte solution for a lithium secondary battery according to the present technology includes: a lithium salt; an organic solvent; and a first additive, and the first additive includes a compound represented by following Chemical formula 1:

[Chemical formula 1]

$$R_1\text{-O-C(=O)-C}(R_2)\text{-CH}_2\text{-O-C(=O)-O-CH}_2$$

Herein, $R_1$ is a substituted or unsubstituted unsaturated hydrocarbon group having 2 to 20 carbon atoms, and $R_2$ is one selected from the group consisting of a substituted or unsubstituted alkyl group having 1 to 10 carbon atoms and a substituted or unsubstituted cyclic alkyl group having 3 to 8 carbon atoms.

11 Claims, No Drawings

NON-AQUEOUS ELECTROLYTE SOLUTION FOR LITHIUM SECONDARY BATTERY

CROSS-REFERENCE TO RELATED APPLICATIONS

The present application is a national stage entry under 35 U.S.C. § 371 of International Application No. PCT/KR2021/016905 filed on Nov. 17, 2021, which claims priority from Korean Patent Application No. 10-2021-0073895 filed on Jun. 8, 2021, all the disclosures of which are incorporated herein by reference.

TECHNICAL FIELD

The present invention relates to a non-aqueous electrolyte solution for a lithium secondary battery, and a lithium secondary battery including the same.

BACKGROUND ART

Recently, the interest in developing energy storage technology is on the increase, and as the applied fields are expanded to mobile phones, camcorders and laptop PCs, and electric vehicles, efforts on the research and development of electrochemical elements are currently embodied.

Among electrochemical devices, the interest in the development of secondary batteries is on the increase, and particularly, lithium secondary batteries developed in 1990s have been spotlighted with the advantages that the operating voltage is high and the energy density is large.

In the case of a lithium secondary battery system, unlike an initial period when lithium metal was directly applied to a system, a transition metal oxide containing lithium is used as the positive electrode material, and carbon-based materials such as graphite and alloy-based materials such as silicon are applied to the negative electrode as the negative electrode material. In this way, a system, in which lithium metal is not directly used in a battery, is currently implemented.

Such a lithium secondary battery is composed of a positive electrode composed of a transition metal oxide containing lithium, a negative electrode capable of storing lithium, an electrolyte solution used for transferring lithium ions, and a separator. Herein, the electrolyte solution is known as a component which significantly affects the stability and safety of the battery, and a lot of researches on the electrolyte solution are currently conducted.

An electrolyte solution for a lithium secondary battery is composed of a lithium salt, an organic solvent which dissolves the lithium salt, and a functional additive. Herein, in order to improve electrochemical characteristics of the battery, it is important to appropriately select these components.

In this regard, in the case of the conventional electrolyte solution, the reductive cleavage stability of the electrolyte solution solvent is low, thereby causing lifespan reduction and electrolyte decomposition during storage. The decomposition reaction of the electrolyte solution forms an SEI film, which acts as a resistive layer, on the interface between the negative electrode and the electrolyte solution, and at the same time generates gas, thereby promoting performance deterioration of the battery.

Further, when the interface between the negative electrode and the electrolyte is unstable, the electrolyte depletion may occur due to the electrolyte decomposition, which may cause degeneration and breakdown of the battery due to lithium precipitation or transition metal precipitation. Further, precipitation of such metal elements act as media which further promote decomposition of the electrolyte.

Particularly, in the case of a negative electrode containing silicon, a SEI film is broken due to the volume change during the charge and discharge, which exposes an unstable negative electrode surface, thereby further promoting electrolyte consumption.

Therefore, there is a need for a technology capable of improving interface stability between electrolyte and a negative electrode.

DISCLOSURE

Technical Problem

The present invention is believed to solve at least some of the above problems. For example, an aspect of the present invention provides a non-aqueous electrolyte solution for a lithium secondary battery, which is capable of improving lifespan characteristics at a room temperature and a high temperature by relieving the decomposition phenomenon of an electrolyte solution during the charge and discharge by securing the stability of the negative electrode-electrolyte interface.

Technical Solution

A non-aqueous electrolyte solution for a lithium secondary battery according to the present invention includes: a lithium salt; an organic solvent; and a first additive, and the first additive includes a compound represented by following chemical formula 1:

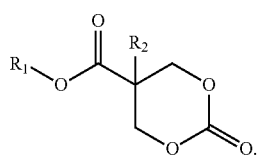

[Chemical formula 1]

Herein, $R_1$ is a substituted or unsubstituted unsaturated hydrocarbon group having 2 to 20 carbon atoms, and $R_2$ is one selected from the group consisting of hydrogen, a substituted or unsubstituted alkyl group having 1 to 10 carbon atoms and a substituted or unsubstituted cyclic alkyl group having 3 to 8 carbon atoms.

In a specific example, $R_1$ may be a substituted or unsubstituted alkenyl group having 2 to 20 carbon atoms, or a substituted or unsubstituted alkynyl group having 2 to 20 carbon atoms.

More specifically, the first additive may be at least one selected from the group consisting of a compound represented by following chemical formula 1a and a compound represented by following chemical formula 1b:

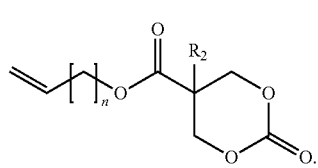

[Chemical formula 1a]

Herein, the n is a natural number between 1 and 18, and $R_2$ is one selected from the group consisting of hydrogen, a substituted or unsubstituted alkyl group having 1 to 10 carbon atoms and a substituted or unsubstituted cyclic alkyl group having 3 to 8 carbon atoms.

[Chemical formula 1b]

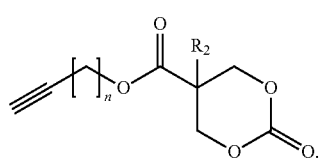

Herein, the n is a natural number between 1 and 18, and $R_2$ is one selected from the group consisting of hydrogen, a substituted or unsubstituted alkyl group having 1 to 10 carbon atoms and a substituted or unsubstituted cyclic alkyl group having 3 to 8 carbon atoms.

More specifically, the first additive may be at least one selected from the group consisting of a compound represented by following chemical formula 1c and a compound represented by following chemical formula 1d:

[Chemical formula 1c]

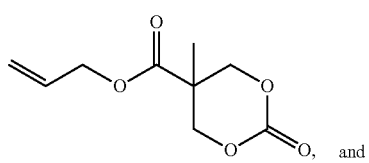

, and

[Chemical formula 1d]

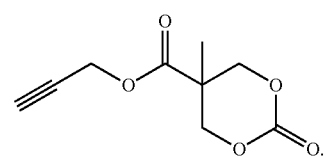

Further, the first additive may include both the compound represented by the chemical formula 1a and the compound represented by the chemical formula 1b, and a molar ratio of the compound represented by the chemical formula 1a to the compound represented by the chemical formula 1b may be in a range of 2:8 to 8:2.

In a specific example, a content of the first additive may correspond to 0.01 to 5 wt % of a total weight of the electrolyte solution.

More specifically, a content of the first additive may correspond to 0.1 to 3 wt % of a total weight of the electrolyte solution.

Further, the non-aqueous electrolyte solution according to the present invention may further include at least one second additive selected from the group consisting of a halogen-substituted or unsubstituted cyclic carbonate compound, a nitrile compound, a phosphate compound, a borate compound, a sultone compound, a lithium salt compound, and a sulfate compound.

Further, the lithium salt may be at least one selected from the group consisting of $LiPF_6$, $LiAsF_6$, $LiN(SO_2F)_2$, $LiCF_3SO_3$, $LiN(CF_3SO_2)_2$, $LiBF_6$, $LiSbF_6$, $LiN(C_2F_5SO_2)_2$, $LiAlO_4$, $LiAlCl_4$, $LiSO_3CF_3$ and $LiClO_4$.

Further, the organic solvent may contain linear carbonate, cyclic carbonate, ester, ether, ketone, or a combination thereof.

The present invention provides a lithium secondary battery including the above-described non-aqueous electrolyte solution for a lithium secondary battery.

Advantageous Effects

The non-aqueous electrolyte solution for a lithium secondary battery according to the present invention may improve the stability of the negative electrode-electrolyte interface by forming a carbon-oxygen single bond or double bond-based film, and improve lifespan characteristics at a room temperature and a high temperature by relieving the decomposition phenomenon of an electrolyte solution during the charge and discharge.

DETAILED DESCRIPTION OF THE PREFERRED EMBODIMENTS

Hereinafter, the present invention will be described in detail. The terms and words used in the present specification and claims should not be construed as limited to ordinary or dictionary terms and the inventor may properly define the concept of the terms in order to best describe its invention. The terms and words should be construed as meaning and concept consistent with the technical idea of the present invention.

In this application, it should be understood that terms such as "include" or "have" are intended to indicate that there is a feature, number, step, operation, component, part, or a combination thereof described in the specification, and they do not exclude in advance the possibility of the presence or addition of one or more other features or numbers, steps, operations, components, parts or combinations thereof. Also, when a portion such as a layer, a film, an area, a plate, etc. is referred to as being "on" another portion, this includes not only the case where the portion is "directly on" the another portion but also the case where further another portion is interposed therebetween. On the other hand, when a portion such as a layer, a film, an area, a plate, etc. is referred to as being "under" another portion, this includes not only the case where the portion is "directly under" the another portion but also the case where further another portion is interposed therebetween. In addition, to be disposed "on" in the present application may include the case disposed at the bottom as well as the top.

Further, in the wording "carbon number a to b" of the present specification, "a" and "b" means the number of carbon atoms included in a specific functional group. Namely, the functional group may include a to b carbon atoms. For example, "alkylene group of carbon number 1 to 5" means an alkylene group having 1 to 5 carbon atoms, namely, —$CH_2$—, —$CH_2CH_2$—, —$CH_2CH_2CH_2$—, —$CH_2CH(CH_3)$—, —$CH(CH_3)CH_2$— and —$CH(CH_3)CH_2CH_2$—, etc.

Hereinafter, the present invention will be described in detail.

Non-Aqueous Electrolyte Solution for Lithium Secondary Battery

A non-aqueous electrolyte solution for a lithium secondary battery according to the present invention includes: a lithium salt; an organic solvent; and a first additive, and the first additive includes a compound represented by following chemical formula 1:

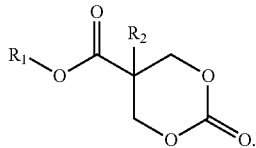

Herein, $R_1$ is a substituted or unsubstituted unsaturated hydrocarbon group having 2 to 20 carbon atoms, and $R_2$ is one selected from the group consisting of a substituted or unsubstituted alkyl group having 1 to 10 carbon atoms and a substituted or unsubstituted cyclic alkyl group having 3 to 8 carbon atoms.

(1) Lithium Salt

In the non-aqueous electrolyte solution for a lithium secondary battery according to an embodiment of the present invention, the lithium salt contains $LiPF_6$, and what is generally used in the electrolyte solution for a lithium secondary battery in addition to $LiPF_6$ may be used without limitation. For example, $Li^+$ is included as the cation of the lithium salt, and at least one selected from the group consisting of $F^-$, $Cl^-$, $Br^-$, $I^-$, $NO_3^-$, $N(CN)_2^-$, $ClO_4^-$, $BF_4^-$, $B_{10}Cl_{10}^-$, $PF_6^-$, $CF_3SO_3^-$, $CH_3CO_2^-$, $CF_3CO_2^-$, $AsF_6^-$, $SbF_6^-$, $AlCl_4^-$, $AlO_4^-$, $CH_3SO_3^-$, $BF_2C_2O_4^-$, $BC_4O_8^-$, $PF_4C_2O_4^-$, $PF_2C_4O_8^-$, $(CF_3)_2PF_4^-$, $(CF_3)_3PF_3^-$, $(CF_3)_4PF_2^-$, $(CF_3)_5PF^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $SCN^-$ and $(CF_3CF_2SO_2)_2N^-$ may be included as the anion.

Specifically, the lithium salt may contain one or a combination of two or more selected from the group consisting of LiCl, LiBr, LiI, $LiClO_4$, $LiBF_4$, $LiB_{10}Cl_{10}$, $LiPF_6$, $LiCF_3SO_3$, $LiCH_3CO_2$, $LiCF_3CO_2$, $LiAsF_6$, $LiSbF_6$, $LiAlCl_4$, $LiAlO_4$, $LiCH_3SO_3$, LiFSI (lithium fluorosulfonyl imide, $LiN(SO_2F)_2$), LiTFSI (lithium (bis)trifluoromethanesulfonimide, $LiN(SO_2CF_3)_2$) and LiBETI (lithium bisperfluoroethanesulfonimide, $LiN(SO_2C_2F_5)_2$). More specifically, the lithium salt may be at least one selected from the group consisting of $LiPF_6$, $LiAsF_6$, $LiCF_3SO_3$, $LiN(CF_3SO_2)_2$, $LiBF_6$, $LiSbF_6$, $LiN(C_2F_5SO_2)_2$, $LiAlO_4$, $LiAlCl_4$, $LiSO_3CF_3$ and $LiClO_4$.

The lithium salt can be appropriately changed within a typically available range, but specifically, 0.1M to 3M lithium salt and more specifically 0.8M to 2.5M lithium salt may be included in the electrolyte solution. If the concentration of the lithium salt exceeds 3M, the viscosity of the non-aqueous electrolyte solution is increased, and the lithium ion transfer effect is lowered and the non-aqueous electrolyte solution wettability is lowered, so that it is difficult to form a SEI film having a uniform thickness on the surface of the electrode.

(2) Organic Solvent

The organic solvent may be minimized in decomposition by oxidation reaction during the charge/discharge of the secondary battery, and there is no limit to the kind of the organic solvent as long as it can show desired characteristics together with the additive. For example, the organic solvent may contain linear carbonate, cyclic carbonate, ester, ether, ketone, or a combination thereof.

Specifically, the cyclic carbonate-based organic solvent may include at least one selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate and fluoroethylene carbonate (FEC), and may specifically include a mixed solvent of ethylene carbonate having a high dielectric constant, and propylene carbonate having a relatively low melting point, compared to ethylene carbonate.

Further, the linear carbonate-based organic solvent is a solvent having a low viscosity and a low dielectric constant and may include at least one selected from the group consisting of dimethyl carbonate (DMC), diethyl carbonate (DEC), dipropyl carbonate, ethyl methyl carbonate (EMC), methylpropyl carbonate, and ethylpropyl carbonate, and may specifically include dimethyl carbonate.

In addition, as the ether-based organic solvent, any one selected from the group consisting of dimethyl ether, diethyl ether, dipropyl ether, methylethyl ether, methylpropyl ether, and ethylpropyl ether, or a mixture of two or more thereof may be used, but is not limited thereto.

The ester-based organic solvent may be at least one selected from the group consisting of a linear ester-based organic solvent and a cyclic ester-based organic solvent.

At this time, one or a mixture of two or more selected from the group consisting of methyl acetate, ethyl acetate, propyl acetate, methyl propionate, ethyl propionate, propyl propionate, and butyl propionate may be used as the linear ester-based organic solvent, but the present invention is not limited to these examples.

One or a mixture of two or more selected from the group consisting of γ-butyrolactone, γ-valerolactone, γ-caprolactone, σ-valerolactone, and ε-caprolactone may be used as the cyclic ester-based organic solvent, but the present invention is not limited to these examples.

A cyclic carbonate-based organic solvent having a high viscosity capable of easily dissociating lithium salt in the electrolyte due to a high dielectric constant may be used as the organic solvent. Further, in order to manufacture an electrolyte having a higher electrical conductivity, a linear carbonate compound and a linear ester compound having a low viscosity and a low dielectric constant, such as dimethyl carbonate and diethyl carbonate, may be mixed together with the cyclic carbonate-based organic solvent at an appropriate ratio.

More specifically, the organic solvent may be obtained by mixing the cyclic carbonate compound with the linear carbonate compound, and the weight ratio of the cyclic carbonate compound and the linear carbonate compound may be in the range of 10:90 to 70:30.

(3) First Additive

Further, the non-aqueous electrolyte solution for a secondary battery of the present invention may further include a first additive comprising a compound represented by following chemical formula 1.

[Chemical formula 1]

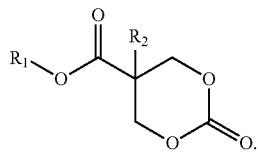

Herein, $R_1$ is a substituted or unsubstituted unsaturated hydrocarbon group having 2 to 20 carbon atoms, and $R_2$ is one selected from the group consisting of hydrogen, a substituted or unsubstituted alkyl group having 1 to 10 carbon atoms and a substituted or unsubstituted cyclic alkyl group having 3 to 8 carbon atoms.

Specifically, $R_1$ may be a substituted or unsubstituted alkenyl group having 2 to 20 carbon atoms, or a substituted or unsubstituted alkynyl group having 2 to 20 carbon atoms. Specifically, the $R_1$ may be an alkenyl group or alkynyl group having 2 to 16, 2 to 12, 2 to 8 or 3 to 5 carbon atoms, and the $R_2$ may be an alkyl group having 1 to 8, 1 to 6, 1 to 4 or 1 to 3 carbon atoms or a cyclic alkyl group having 3 to 6 carbon atoms.

Further, in the chemical formula 1, the $R_1$ may be a terminal alkenyl group or a terminal alkynyl group. Herein, the terminal alkenyl group refers to what a double bond has been formed at the terminal of the chain, and the terminal alkynyl group refers to what a triple bond has been formed at the terminal of the chain.

Specifically, the first additive may be at least one selected from the group consisting of a compound represented by following chemical formula 1a and a compound represented by following chemical formula 1b:

[Chemical formula 1a]

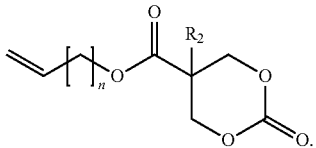

Herein, the n is a natural number between 1 and 18, and $R_2$ is one selected from the group consisting of hydrogen, a substituted or unsubstituted alkyl group having 1 to 10 carbon atoms and a substituted or unsubstituted cyclic alkyl group having 3 to 8 carbon atoms.

[Chemical formula 1b]

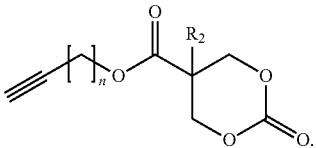

Herein, the n is a natural number between 1 and 18, and $R_2$ is one selected from the group consisting of hydrogen, a substituted or unsubstituted alkyl group having 1 to 10 carbon atoms and a substituted or unsubstituted cyclic alkyl group having 3 to 8 carbon atoms.

In the chemical formulas 1a and 1b, the n may be in a range of 1 to 18, 1 to 14, 1 to 10, 1 to 6, or 1 to 3.

Nonlimiting examples of such compounds include 5-Methyl-5-allyloxycarbonyl-1,3-dioxan-2-one (MACBD) represented by chemical formula 1c, and 5-Methyl-5-propargyloxycarbonyl-1,3-dioxan-2-one (MPCBD) represented by chemical formula 1d.

[Chemical formula 1c]

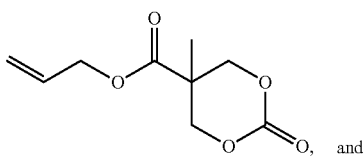

and

[Chemical formula 1d]

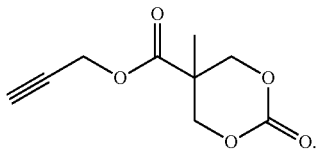

The compound represented by the chemical formula 1 contains an ester functional group and an unsaturated hydrocarbon group in a molecular structure, and forms a film which uses a carbon-oxygen single bond (C—O) or carbon-oxygen double bond (C=O)-based compound as main constituents. Further, since the first additive contains an unsaturated hydrocarbon functional group such as an allyl group and a propargyl group, it is easy to be reduced on the surface of the negative electrode, and a film can be easily formed on the surface of the negative electrode. Such a film has a stability higher than that of the SEI film formed by a general reductive decomposition of the electrolyte solution, and suppresses additional electrolyte solution decomposition reactions due to a low electronic conductivity and is not easily damaged by the volume change of the negative electrode. Namely, it is possible to secure stability of the interface between the negative electrode and the electrolyte solution by using the compound like the chemical formula 1 as the additive of the electrolyte solution.

At this time, a compound including a terminal alkenyl group like the chemical formula 1a or a compound including a terminal alkynyl group like the chemical formula 1b may be solely used as the first additive, but the mixture of these two compounds may also be used. Likewise, in the case that the first additive includes both the compound represented by the chemical formula 1a and the compound represented by the chemical formula 1b, the molar ratio of the compound represented by the chemical formula 1a to the compound represented by the chemical formula 1b may be in a range of 2:8 to 8:2, 3:7 to 7:3, or 4:6 to 6:4.

Further, in the present invention, the content of the first additive may correspond to 0.01 to 5 wt %, specifically 0.1 to 3 wt %, and more specifically 0.5 to 2 wt % of the total weight of the electrolyte solution. When the content of the first additive is in the above range, it is possible to form a stable film while not increasing the resistance of the battery.

When the content of the first additive is less than 0.01 wt %, it is difficult to achieve desired effects, and when the content of the first additive exceeds 5 wt %, the additive is not sufficiently decomposed, and the additive may act as the resistance, thereby decreasing the performance of the battery.

(4) Second Additive

Further, the non-aqueous electrolyte solution for a lithium secondary battery according to the present invention may further include a second additive capable of showing the effect manifested by the mixed additive, and functioning as a complement which can form a stable film on the surface of the negative electrode and the positive electrode, or suppress decomposition by side reaction of the solvent in the non-aqueous electrolyte solution and improve mobility of lithium ions while not significantly increasing the initial resistance.

Specifically, the non-aqueous electrolyte solution according to the present invention may further include at least one additive selected from the group consisting of a halogen-substituted or unsubstituted cyclic carbonate compound, a nitrile compound, a phosphate compound, a borate compound, a sultone compound, a lithium salt compound, and a sulfate compound.

Specifically, the halogen-substituted cyclic carbonate compound or the halogen-unsubstituted cyclic carbonate compound may improve durability of the battery by forming a stable SEI film on the surface of the negative electrode during battery activation.

Fluoroethylene carbonate (FEC) may be used as the halogen-substituted cyclic carbonate compound. Further, examples of the unsubstituted cyclic carbonate compound may include vinylene carbonate (VC) and vinyl ethylene carbonate (VEC).

The content of the halogen-substituted cyclic carbonate compound or the halogen-unsubstituted cyclic carbonate compound may correspond to 8 wt % or less and specifically 5 wt % or less of the total weight of the non-aqueous electrolyte solution. When the content of the cyclic carbonate compound in the non-aqueous electrolyte solution exceeds 8 wt %, the cell swelling suppressing performance and initial resistance may be deteriorated.

When the nitrile compound is used together with the above-described mixed additive, effects of improvement of high temperature characteristics, etc. can be expected by positive/negative electrode film stabilization. Namely, it may act as a supplementary element in forming a negative electrode SEI film, suppress decomposition of a solvent in the electrolyte, and improve mobility of lithium ions. Examples of the nitrile compound may include at least one selected from the group consisting of succinonitrile, adiponitrile, acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, 4-fluorophenylacetonitrile, 1,4-dicyano-2-butene, glutaronitrile, 1,3,6-hexanetricarbonitrile, and pimelonitrile.

The content of the nitrile compound may correspond to 8 wt % or less and specifically 5 wt % or less of the total weight of the non-aqueous electrolyte solution. When the total content of the nitrile compound in the non-aqueous electrolyte solution exceeds 8 wt %, the resistance increases due to the increase of the film formed on the surface of the electrode, thereby deteriorating the performance of the battery.

Further, since the phosphate compound stabilizes $PF_6$ anions in the electrolyte solution and helps formation of a positive electrode and negative electrode film, thereby improving durability of the battery. Some examples of the phosphate-based compounds may include at least one selected from the group consisting of lithium difluoro (bisoxalato) phosphate (LiDFOP), lithium difluorophosphate (LiDFP, $LiPO_2F_2$), lithium tetramethyl trimethyl silyl phosphate, trimethyl silyl phosphite (TMSPi), trimethyl silyl phosphate (TMSPa), ethyl di(prop-2-yn-1-yl)phosphate, allyl diphosphate, tris(2, 2,2-trifluoroethyl) phosphate (TFEPa) and tris(trifluoroethyl) phosphite, and the content of the phosphate-based compound may correspond to 3 or less wt % and specifically 1 or less wt % of the total weight of the non-aqueous electrolyte solution.

The borate compound may improve mobility of the lithium ions by promoting ion pair separation, lower the interface resistance of the SEI film, and may solve problems such as hydrofluoric acid gas generation by dissociating materials such as LiF, which are generated during battery reaction and are not easily separated. LiBOB, $LiB(C_2O_4)_2$, lithium oxalyldifluoroborate, or tetramethyl trimethylsilyl-borate (TMSB) may be used as the borate compound, and the content of the borate compound may be 3 wt % or less and specifically 1 wt % or less of the total weight of the non-aqueous electrolyte solution.

At least one compound selected from the group consisting of 1,3-propane sultone (PS), 1,4-butane sultone, ethane sultone, 1,3-propene sultone (PRS), 1,4-butene sultone, and 1-methyl-1,3-propene sultone may be used as the sultone compound, and the content of the sultone compound may be in the range of 0.3 to 5 wt % and specifically 1 to 5 wt % of the total weight of the non-aqueous electrolyte solution. When the content of the sultone-based compound in the non-aqueous electrolyte solution exceeds 5 wt %, an excessively thick film may be formed on the surface of the electrode, thereby increasing the resistance and deteriorating the output, and the resistance may increase by a large amount of additives in the non-aqueous electrolyte solution, thereby deteriorating the output characteristics.

Further, the lithium salt-based compound is a compound which is different from a lithium salt contained in the non-aqueous electrolyte solution. Some examples of the lithium salt-based compound include one or more selected from the group consisting of lithium methylsulfate, lithium ethylsulfate, lithium 2-trifluoromethyl-4,5-dicyanoimidazole, lithium tetrafluorooxalatophosphate, LiODFB and $LiBF_4$, and the content of the lithium salt-based compound may correspond to 3 wt % or less and specifically 1 wt % or less of the total weight of the non-aqueous electrolyte solution.

Further, some examples of the sulfate compound may include ethylene sulfate, trimethylene sulfate (TMS), and methyltrimethylene sulfate (MTMS), and the content of the sulfate compound may correspond to 3 wt % or less and specifically 1 wt % or less of the total weight of the non-aqueous electrolyte solution.

More specifically, the second additive may include one or a combination of two or more selected from the group consisting of vinyl ethylene carbonate, fluoroethylene carbonate, 1,3-propane sultone, and lithium oxalyldifluoroborate (ODFB).

Two or more kinds of additives can be mixed and used, the content of the second additives may correspond to 20 or less wt %, preferably 0.01 to 15 wt %, and more preferably 0.1 to 10 wt % of the total weight of the electrolyte solution.

When the content of additives, which may be additionally added, is less than 0.01 wt %, high temperature storage characteristics and gas reduction effects, which are intended to be implemented from the additive, are very weak, and if the content exceeds 20 wt %, the side reaction may excessively occur. In particular, when a large amount of additives are added, they may not be sufficiently decomposed and may remain in a precipitated or unreacted state in the electrolyte solution at a room temperature. As such, the resistance increases, and the lifespan characteristics of the secondary battery may be deteriorated.

Lithium Secondary Battery

Further, in an embodiment of the present invention, a lithium secondary battery including a non-aqueous electrolyte solution for a secondary battery of the present invention is provided.

A lithium secondary battery of the present invention includes: a positive electrode; a negative electrode; a separator; and the above-described non-aqueous electrolyte solution for a lithium secondary battery. Specifically, the lithium secondary battery can be manufactured by injecting the non-aqueous electrolyte solution of the present invention into an electrode assembly which is obtained as a positive electrode, a negative electrode, and a separator interposed between the positive electrode and the negative electrode are sequentially laminated. At this time, a positive electrode, a negative electrode and a separator, which have been commonly used in manufacturing a lithium secondary battery, may be used as the positive electrode, the negative electrode, and the separator which form an electrode assembly.

Further, the positive electrode and the negative electrode, which form a lithium secondary battery of the present invention, can be manufactured in a general method and used.

(1) Positive Electrode

The positive electrode may be manufactured by forming a positive electrode mixture layer on a positive electrode current collector. The positive electrode mixture layer can be formed by coating a positive electrode slurry, which includes a positive electrode active material, a binder, a conductive material, and a solvent, on a positive electrode current collector, and then drying the slurry and rolling the positive electrode current collector.

The positive electrode current collector is not particularly limited as long as it has conductivity without causing a chemical change in the battery. Examples of the positive electrode current collector include stainless steel, aluminum, nickel, titanium, sintered carbon or aluminum or stainless steel of which the surface has been treated with carbon, nickel, titanium, silver, or the like.

The positive electrode active material is a compound capable of reversible intercalation and deintercalation of lithium, and may specifically include a lithium metal oxide containing lithium and at least one metal such as cobalt, manganese, nickel or aluminum. Specifically, some examples of the lithium metal oxide may include lithium-nickel-manganese-cobalt-based oxide (e.g., $Li(Ni_p Co_q Mn_{r1})O_2$ (herein, $0<p<1$, $0<q<1$, $0<r1<1$, $p+q+r1=1$), or $Li(Ni_{p1} Co_{g1} Mn_{r2})O_4$ (herein, $0<p1<2$, $0<q1<2$, $0<r2<2$, $p1+q1+r2=2$), etc.), or lithium-nickel-cobalt-transition metal (M) oxide (e.g., $Li(Ni_{p2} Co_{q2} Mn_{r3} M_{s2})O_2$ (herein, M is one selected from the group consisting of Al, Fe, V, Cr, Ti, Ta, Mg and Mo, and p2, q2, r3 and s2 are atomic fractions of respectively independent elements, and $0<p2<1$, $0<q2<1$, $0<r3<1$, $0<s2<1$, $p2+q2+r3+s2=1$), etc.).

Examples of the positive electrode active material may include $Li(Ni_{1/3} Mn_{1/3} Co_{1/3})O_2$, $Li(Ni_{0.35} Mn_{0.28} Co_{0.37})O_2$, $Li(Ni_{0.6} Mn_{0.2} Co_{0.2})O_2$, $Li(Ni_{0.5} Mn_{0.3} Co_{0.2})O_2$, $Li(Ni_{0.7} Mn_{0.15} Co_{0.15})O_2$, $Li(Ni_{0.5} Mn_{0.1} Co_{0.1})O_2$ or $Li(Ni_{0.5} Co_{0.15} Al_{0.05})O_2$.

The content of the positive electrode active material may correspond to 90 to 99 wt % and specifically 93 to 98 wt % of the total weight of solids in the positive electrode slurry.

The binder is added in an amount of 1 to 30% by weight, on the basis of the total weight of solids in the positive electrode slurry, as a component that assists in bonding between the active material and the conductive material and bonding to the current collector. Examples of such binders include polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, ethylene-propylene-diene terpolymer, sulfonated ethyl-propylene-diene terpolymer, styrene butadiene rubber, fluorine rubber, and various copolymers.

Such a conductive material is not particularly limited as long as it has electrical conductivity without causing a chemical change in the battery, and examples thereof include: carbon powders such as carbon black, acetylene black, Ketjen black, channel black, furnace black, lamp black, or summer black; graphite powders such as natural graphite or artificial graphite, or graphite, of which the crystal structure has been very much developed; conductive fibers such as carbon fiber and metal fiber; conductive powders such as carbon fluoride, aluminum and nickel powder; conductive whiskey such as zinc oxide and potassium titanate; conductive metal oxides such as titanium oxide; and conductive materials such as polyphenylene derivatives and the like.

The conductive material is usually added in an amount of 1 to 30% by weight based on the total weight of solids in the positive electrode slurry.

The solvent may include an organic solvent such as NMP (N-methyl-2-pyrrolidone), and may be used in an amount that becomes a desirable viscosity when the positive electrode active material and optionally a binder and a conductive material are included. For example, the concentration of the positive electrode active material and, optionally, the solids in the slurry including the binder and the conductive material may be included in an amount of 10 wt % to 70 wt %, preferably 20 wt % to 60 wt %.

(2) Negative Electrode

The negative electrode may be manufactured by forming a negative electrode mixture layer on a negative electrode current collector. The negative electrode mixture layer may be formed by coating a slurry including a negative electrode active material, a binder, a conductive material, a solvent, and the like on a negative electrode current collector, followed by drying and rolling.

The negative electrode current collector is generally made to a thickness of 3 to 500 micrometers. The negative electrode current collector is not particularly limited as long as it has high electrical conductivity without causing chemical changes in the battery, and examples thereof include copper, stainless steel, aluminum, nickel, titanium, sintered carbon, copper or stainless steel of which the surface has been treated with carbon, nickel, titanium, silver or the like, aluminum-cadmium alloy, or the like. In addition, like the positive electrode current collector, fine unevenness can be formed on the surface to enhance the bonding force of the negative electrode active material, and it can be used in various forms such as a film, a sheet, a foil, a net, a porous body, a foam, and a nonwoven fabric.

Further, the negative electrode active material may include at least one selected from the group consisting of lithium metal, a carbon material capable of reversibly intercalating/deintercalating lithium ions, metal or an alloy of a metal and lithium, a metal oxide, a material capable of doping and dedoping lithium, and a transition metal oxide.

Any carbon-based negative electrode active material, which is generally used in a lithium ion secondary battery, may be used as a carbon material capable of reversibly intercalating/deintercalating the lithium ions, and representative examples thereof may include crystalline carbon, amorphous carbon, or a combination thereof. Some examples of the crystalline carbon may include amorphous, flaky, spherical, or fibrous natural graphite or artificial graphite, and some examples of the amorphous carbon may include soft carbon, hard carbon, mesophase pitch carbide, and calcined coke.

A metal selected from the group consisting of Cu, Ni, Na, K, Rb, Cs, Fr, Be, Mg, Ca, Sr, Si, Sb, Pb, In, Zn, Ba, Ra, Ge, Al and Sn, or an alloy of lithium and these metals may be used.

One selected from the group consisting of PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, $Bi_2O_5$, $Li_xFe_2O_3 (0 \leq x \leq 1)$, $Li_xWO_2 (0 \leq x \leq 1)$, and $Sn_xMe_{1-x}Me'_yO_z$ (Me: Mn, Fe, Pb, Ge; Me': Al, B, P, Si, group 1, group 2 and group 3 elements of the periodic table, halogen; $0<x\le1$; $1\le y\le3$; $1\le z\le8$) may be used as the metal oxide.

Some examples of materials capable of doping and dedoping the lithium may include Si, $SiO_x(0<x<2)$, Si—Y alloy (Y is one selected from the group consisting of alkali metal, alkali earth metal, group 13 element, group 14 element, transition metal, rare earth element, and is not Si), Sn, $SnO_2$, Sn—Y (Y is one selected from the group consisting of alkali metal, alkali earth metal, group 13 element, group 14 element, transition metal, rare earth element, and is not Sn), and at least one of them may be mixed with $SiO_2$. One selected from the group consisting of Mg, Ca, Sr, Ba, Ra, Sc, Y, Ti, Zr, Hf, Rf, V, Nb, Ta, db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Ti, Ge, P, As, Sb, Bi, S, Se, Te, Po, and a combination thereof may be used as the element Y.

Examples of the transition metal oxide include lithium-containing titanium oxide (LTO), vanadium oxide, lithium vanadium oxide, and the like.

The negative electrode active material may be included in 80% by weight to 99% by weight based on the total weight of solids in the negative electrode slurry.

In the negative electrode, the binder and the conductive material, which have been used in the above-described positive electrode, may be used.

The solvent may include an organic solvent such as water, NMP or alcohol, and may be used in an amount that becomes a desirable viscosity when the negative electrode active material and optionally a binder and a conductive material are included. For example, the concentration of the negative electrode active material and, optionally, the solids in the slurry including the binder and the conductive material may be included in an amount of 50 wt % to 75 wt %, preferably 50 wt % to 65 wt %.

(3) Separator

An organic separator or an organic and inorganic composite separator can be used as the separator.

A porous polymer film, which is prepared by a polyolefin-based polymer such as ethylene homopolymer, propylene homopolymer, ethylene/butene copolymer, ethylene/hexene copolymer, and ethylene/methacrylate copolymer, may be used alone, or a laminate thereof may be used as the organic separator. Alternatively, a general porous non-woven fabric such as a non-woven fabric made of a glass fiber having a high melting point, a polyethylene terephthalate fiber, etc. may be used as the organic separator.

An organic/inorganic complex porous safety-reinforcing separator (SRS), which is obtained as a porous coating layer containing inorganic particles and a binder polymer is applied on the porous polyolefin-based separator substrate, may be used as the organic and inorganic complex separator.

Inorganic particles having lithium ion transfer capability or mixtures thereof are preferably used as the inorganic particles, and some examples of the inorganic particles include one or a mixture of two or more selected from the group consisting of $BaTiO_3$, $BaTiO_3$, $Pb(Zr,Ti)O_3$ (PZT), $Pb_{1-x}La_xZr_{1-y}Ti_yO_3$ (PLZT, herein, $0<x<1$, $0<y<1$), hafnia ($HfO_2$), $SrTiO_3$, $SnO_2$, $CeO_2$, MgO, NiO, CaO, ZnO, $ZrO_2$, $Y_2O_3$, $Al_2O_3$, $TiO_2$, SiC, and a mixture thereof.

The outer shape of the lithium secondary battery of the present invention is not particularly limited, but the lithium secondary battery may have a cylindrical shape using a can, a prismatic shape, a pouch shape or a coin shape.

Hereinafter, the present invention will be described in detail with reference to examples. However, the embodiments according to the present invention may be modified into various other forms, and the scope of the present invention should not be construed as being limited to the examples described below. The examples of the present invention are provided to more fully describe the present invention to those skilled in the art.

Example 1

<Preparation of Non-Aqueous Electrolyte Solution>

A non-aqueous organic solvent was manufactured by mixing ethylene carbonate (EC), propylene carbonate (PC), ethyl propionate (EP) and propyl propionate (PP) at the weight ratio of 20:10:25:45, and $LiPF_6$ was dissolved in the non-aqueous organic solvent to have the concentration of 1.0 M. A non-aqueous electrolyte solution was manufactured by adding 5-Methyl-5-allyloxycarbonyl-1,3-dioxan-2-one (MACBD) of 0.5 wt % as the first additive based on the total weight of the electrolyte solution and mixing them.

<Preparation of Electrode>

A positive electrode active material slurry (50 wt % solids concentration) was manufactured by adding a positive electrode active material ($Li(Ni_{0.6}Mn_{0.2}Co_{0.2})O_2$), a conductive material (carbon black) and a binder (polyvinylidene fluoride) at the weight ratio of 90:5:5, to N-methyl-2-pyrrolidone (NMP) as a solvent. A positive electrode was manufactured by applying the positive electrode active material slurry on a positive electrode current collector (Al film) having a thickness of 10 μm, then drying the slurry and roll-pressing the positive electrode current collector.

A negative electrode active material slurry (60 wt % of solids concentration) was manufactured by adding a negative electrode active material (artificial graphite), a binder (PVDF), and a conductive material (carbon black) at the weight ratio of 95:2:3, to NMP as a solvent. A negative electrode was manufactured by applying the negative electrode active material slurry on a negative electrode current collector (Cu film) having a thickness of 8 μm, then drying the slurry and roll-pressing the negative electrode current collector.

<Preparation of Secondary Battery>

A positive electrode and a negative electrode, which were manufactured in the above-described manner, were sequentially laminated together with a polyethylene porous film, to thereby manufacture an electrode assembly. Thereafter, the electrode assembly was put in a battery case, and the non-aqueous electrolyte solution was injected into the battery case, which was then sealed, to thereby manufacture a lithium secondary battery.

Example 2

A non-aqueous electrolyte solution and a secondary battery were manufactured in the same manner as in the example 1 except that 5-Methyl-5-allyloxycarbonyl-1,3-dioxan-2-one (MACBD) of 1.0 wt % as the first additive was added based on the total weight of the electrolyte solution.

Example 3

A non-aqueous electrolyte solution and a secondary battery were manufactured in the same manner as in the example 1 except that 5-Methyl-5-propargyloxycarbonyl-1, 3-dioxan-2-one (MPCBD) of 0.5 wt % as the first additive was added based on the total weight of the electrolyte solution.

Comparative Example 1

A non-aqueous electrolyte solution and a secondary battery were manufactured in the same manner as in the example 1 except that a first additive was not added to a solvent.

Comparative Example 2

A non-aqueous electrolyte solution and a secondary battery were manufactured in the same manner as in the example 1 except that 5-Methyl-5-allyloxycarbonyl-1,3-dioxan-2-one (MACBD) of 0.005 wt % as the first additive was added based on the total weight of the electrolyte solution.

Comparative Example 3

A non-aqueous electrolyte solution and a secondary battery were manufactured in the same manner as in the example 1 except that 5-Methyl-5-allyloxycarbonyl-1,3-dioxan-2-one (MACBD) of 7 wt % as the first additive was added based on the total weight of the electrolyte solution.

Experimental Example 1: Room Temperature Lifespan Evaluation

The secondary batteries, which were manufactured in the examples and comparative examples, were charged with the constant current/constant voltage up to 4.2V at the rate of 0.5 C at a room temperature (25° C.), and was then discharged up to 2.5V at the rate of 0.5 C. At this time, the charge and discharge was performed using PNE-0506 charge-discharge device (manufacturer: PNE Solution Co., Ltd., 5V, 6A), and the measured discharge capacity was defined as in the initial discharge capacity.

Based on the assumption that the charge and discharge process is one cycle, a total of 200 cycles were performed, and then the measured initial discharge capacity and the discharge capacity after 200 cycles were substituted to the following formula (1) to thereby measure the capacity retention rate, and the result was shown in Table 1 below.

Capacity retention rate (%)=(Discharge capacity after 200 cycles/Initial discharge capacity)×100    Formula (1):

Herein, in the case of the comparative example 3, the evaluation was not possible because the additive was not uniformly dissolved in the electrolyte solution.

TABLE 1

Experimental Example 2 - High temperature storage characteristic evaluation

|  | Initial capacity (mAh/g) | Capacity after 200 times (mAh/g) | Capacity retention rate (%) |
|---|---|---|---|
| Example 1 | 3220.9 | 2769.6 | 86.0 |
| Example 2 | 3215.7 | 2593.4 | 80.6 |
| Example 3 | 3218.5 | 2687.9 | 83.5 |
| Comparative Example 1 | 3224.1 | 2243.9 | 69.6 |
| Comparative Example 2 | 3221.5 | 2293.7 | 71.2 |
| Comparative Example 3 | — | — | — |

The secondary batteries, which were manufactured in the examples and comparative examples, were charged with the constant current/constant voltage up to 4.2V at the rate of 0.5 C at a room temperature (25° C.), and was then discharged up to 2.5V at the rate of 0.5 C. At this time, the charge and discharge was performed using PNE-0506 charge-discharge device (manufacturer: PNE Solution Co., Ltd., 5V, 6A), and the measured discharge capacity was defined as in the initial discharge capacity.

The secondary batteries were stored at the condition of 60° C. for two weeks, and the capacity retention rate was then measured by substituting the discharge capacity measured in the same manner into the following formula (2). The result is shown in Table 2 below.

Capacity retention rate (%)=(Discharge capacity after 2 week storage/Initial discharge capacity)×100    Formula (2):

TABLE 2

Referring to Tables 1 and 2, when an additive like the chemical formula 1 is included

|  | Initial capacity (mAh/g) | Capacity after 200 times (mAh/g) | Capacity retention rate (%) |
|---|---|---|---|
| Example 1 | 3219.9 | 2879.1 | 89.4 |
| Example 2 | 3216.1 | 2746.3 | 85.3 |
| Example 3 | 3219.3 | 2785.9 | 86.5 |
| Comparative Example 1 | 3223.2 | 2431.5 | 75.4 |
| Comparative Example 2 | 3222.6 | 2484.6 | 77.1 |
| Comparative Example 3 | — | — | — | in the electrolyte solution, specifically when an additive having the same structure as that of the chemical formula 1a or 1b is solely used or a mixture of two kinds is used, the capacity retention rate after the charge and discharge of 200 times and the capacity retention rate after a high temperature storage were better than that of the comparative example 1. This is because the stability of the interface between the electrolyte solution and the negative electrode has been improved as a stable SEI film is formed by the additive's reductive decomposition during the charge and discharge. Further, in the case of comparative examples 1 and 2 where the additive has not been added or a very little amount of the additive has been added, the capacity retention rate decreased, compared to the examples. This is because the effects were not obtained due to a small amount of the additive, or the additive acted as a resistance due to the remaining additive.

The above description is merely illustrative of the technical idea of the present invention, and those skilled in the art to which the present invention pertains may make various modifications and variations without departing from the essential characteristics of the present invention. The scope of protection of the present invention should be interpreted by the following claims, and all technical ideas within the scope equivalent thereto should be construed as being included in the scope of the present invention.

On the other hand, in this specification, terms indicating directions such as up, down, left, right, before, and after are used, but it is obvious that these terms are for convenience of description only and may change depending on the location of the object or the location of the observer.

The invention claimed is:

1. A non-aqueous electrolyte solution for a lithium secondary battery, the non-aqueous electrolyte solution comprising: a lithium salt; an organic solvent; and a first additive,
wherein the first additive includes a compound represented by following Chemical formula 1:

[Chemical formula 1]

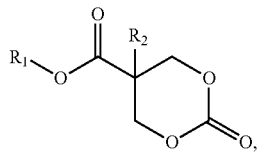

wherein $R_1$ is a substituted or unsubstituted unsaturated hydrocarbon group having 2 to 20 carbon atoms, and $R_2$ is one selected from the group consisting of hydrogen, a substituted or unsubstituted alkyl group having 1 to 10 carbon atoms and a substituted or unsubstituted cyclic alkyl group having 3 to 8 carbon atoms.

2. The non-aqueous electrolyte solution of claim 1, wherein $R_1$ is a substituted or unsubstituted alkenyl group having 2 to 20 carbon atoms, or a substituted or unsubstituted alkynyl group having 2 to 20 carbon atoms.

3. The non-aqueous electrolyte solution of claim 1, wherein the first additive is at least one selected from the group consisting of a compound represented by following Chemical formula 1a and a compound represented by following Chemical formula 1b:

[Chemical formula 1a]

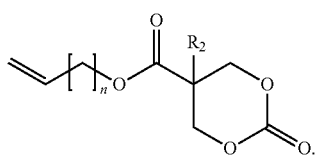

wherein n is an integer between 1 and 18, and $R_2$ is one selected from the group consisting of hydrogen, a substituted or unsubstituted alkyl group having 1 to 10 carbon atoms and a substituted or unsubstituted cyclic alkyl group having 3 to 8 carbon atoms,

[Chemical formula 1b]

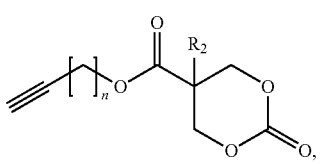

wherein n is an integer between 1 and 18, and $R_2$ is one selected from the group consisting of hydrogen, a substituted or unsubstituted alkyl group having 1 to 10 carbon atoms and a substituted or unsubstituted cyclic alkyl group having 3 to 8 carbon atoms.

4. The non-aqueous electrolyte solution of claim 3, wherein the first additive is at least one selected from the group consisting of a compound represented by following Chemical formula 1c and a compound represented by following Chemical formula 1d:

[Chemical formula 1c]

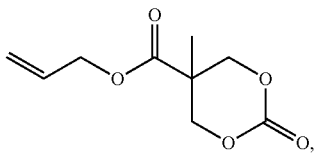

[Chemical formula 1d]

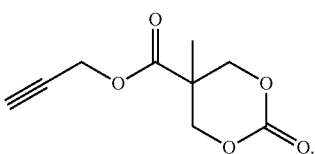

5. The non-aqueous electrolyte solution of claim 3, wherein the first additive includes both the compound represented by Chemical formula 1a and the compound represented by Chemical formula 1b, and a molar ratio of the compound represented by Chemical formula 1a to the compound represented by Chemical formula 1b is in a range of 2:8 to 8:2.

6. The non-aqueous electrolyte solution of claim 1, wherein the first additive is included in an amount of 0.01 to 5 wt % based on a total weight of the electrolyte solution.

7. The non-aqueous electrolyte solution of claim 1, wherein the first additive is included in an amount of 0.1 to 3 wt % based on a total weight of the electrolyte solution.

8. The non-aqueous electrolyte solution of claim 1, further comprising: at least one second additive selected from the group consisting of a halogen-substituted or unsubstituted cyclic carbonate compound, a nitrile compound, a phosphate compound, a borate compound, a sultone compound, a lithium salt compound, and a sulfate compound.

9. The non-aqueous electrolyte solution of claim 1, wherein the lithium salt is at least one selected from the group consisting of $LiPF_6$, $LiAsF_6$, $LiN(SO_2F)_2$, $LiCF_3SO_3$, $LiN(CF_3SO_2)_2$, $LiBF_6$, $LiSbF_6$, $LiN(C_2F_5SO_2)_2$, $LiAlO_4$, $LiAlCl_4$, $LiSO_3CF_3$ and $LiClO_4$.

10. The non-aqueous electrolyte solution of claim 1, wherein the organic solvent contains linear carbonate, cyclic carbonate, ester, ether, ketone, or a combination thereof.

11. A lithium secondary battery including the non-aqueous electrolyte solution for a lithium secondary battery according to claim 1.

* * * * *